US008147813B2

(12) United States Patent
Beauquey et al.

(10) Patent No.: US 8,147,813 B2
(45) Date of Patent: Apr. 3, 2012

(54) DETERGENT COSMETIC COMPOSITIONS COMPRISING THREE SURFACTANTS AND AT LEAST ONE FATTY ESTER, AND USE THEREOF

(75) Inventors: Bernard Beauquey, Clichy (FR); Sandrine Maggio, Vincennes (FR); Sabina Meralli, Vanves (FR)

(73) Assignee: L'Oreal S.A. (FR)

( * ) Notice: Subject to any disclaimer, the term of this patent is extended or adjusted under 35 U.S.C. 154(b) by 684 days.

(21) Appl. No.: 11/392,733

(22) Filed: Mar. 30, 2006

(65) Prior Publication Data

US 2006/0233733 A1    Oct. 19, 2006

Related U.S. Application Data

(60) Provisional application No. 60/669,890, filed on Apr. 11, 2005.

(30) Foreign Application Priority Data

Mar. 30, 2005 (FR) ..................... 05 50808

(51) Int. Cl.
*A61K 8/81*       (2006.01)
*A61K 8/73*       (2006.01)
(52) U.S. Cl. ............... 424/70.13; 424/70.15; 424/70.17
(58) Field of Classification Search .............. None
See application file for complete search history.

(56) References Cited

U.S. PATENT DOCUMENTS

| | | | |
|---|---|---|---|
| 2,528,378 A | 10/1950 | Mannheimer | |
| 2,781,354 A | 2/1957 | Mannheimer | |
| 4,217,914 A | 8/1980 | Jacquet et al. | |
| 4,240,450 A | 12/1980 | Grollier et al. | |
| 4,422,853 A | 12/1983 | Jacquet et al. | |
| 4,445,521 A | 5/1984 | Grollier et al. | |
| 4,719,099 A | 1/1988 | Grollier et al. | |
| 4,839,166 A | 6/1989 | Grollier et al. | |
| 4,948,579 A | 8/1990 | Jacquet et al. | |
| 4,996,059 A | 2/1991 | Grollier et al. | |
| 5,009,880 A | 4/1991 | Grollier et al. | |
| 5,063,052 A * | 11/1991 | Grollier et al. .......... 424/70.121 |
| 5,089,252 A | 2/1992 | Grollier et al. | |
| 5,139,037 A | 8/1992 | Grollier et al. | |
| 5,196,189 A | 3/1993 | Jacquet et al. | |
| 5,955,406 A | 9/1999 | Dubief et al. | |
| 6,284,230 B1 | 9/2001 | Sako et al. | |
| 6,432,908 B1 | 8/2002 | Dubief et al. | |
| 6,589,519 B1 | 7/2003 | Restle et al. | |
| 6,726,902 B1 | 4/2004 | Müller et al. | |
| 7,217,777 B2 | 5/2007 | Lange et al. | |
| 2002/0183217 A1 | 12/2002 | Perron et al. | |
| 2004/0102354 A1* | 5/2004 | Fack et al. ............. 510/466 |
| 2005/0049169 A1* | 3/2005 | Mizushima .............. 510/424 |

FOREIGN PATENT DOCUMENTS

| | | |
|---|---|---|
| DE | 39 29 973 A1 | 3/1991 |
| DE | 197 10 873 A1 | 9/1998 |
| DE | 100 48 449 A1 | 4/2002 |
| DE | 100 48 450 A1 | 4/2002 |
| DE | 600 00 236 T2 | 10/2002 |
| DE | 101 61 885 A1 | 7/2003 |
| DE | 102 61 110 A1 | 7/2004 |
| EP | 0 337 354 B1 | 10/1989 |
| EP | 1 034 775 A1 | 9/2000 |
| EP | 1 064 915 A1 | 1/2001 |
| EP | 1 232 739 A1 | 8/2002 |
| EP | 1 245 225 A2 | 10/2002 |
| EP | 1 250 906 A2 | 10/2002 |
| FR | 2 270 846 | 12/1975 |
| FR | 2 383 660 | 10/1978 |
| FR | 2 470 596 | 6/1981 |
| FR | 2 519 863 | 7/1983 |
| FR | 2 598 611 A1 | 11/1987 |
| JP | H08-040845 | 2/1996 |
| JP | H10-298040 | 11/1998 |
| JP | 2000-095726 | 4/2000 |
| JP | 2000-129300 | 5/2000 |
| JP | 2001-031536 | 2/2001 |

(Continued)

OTHER PUBLICATIONS

French Search Report for FR 0550808, dated Dec. 5, 2005.

(Continued)

*Primary Examiner* — Frederick Krass
*Assistant Examiner* — Brian Gulledge
(74) *Attorney, Agent, or Firm* — Finnegan, Henderson, Farabow, Garrett & Dunner, LLP

(57) ABSTRACT

The present disclosure relates to novel detergent and conditioning compositions comprising, in a cosmetically acceptable medium, at least one sulfate or sulfonate anionic surfactant; at least one carboxylic anionic surfactant chosen from polyoxyalkylenated ($C_6$-$C_{24}$)alkyl ether carboxylic acids, polyoxyalkylenated ($C_6$-$C_{24}$)alkylaryl ether carboxylic acids and salts thereof, polyoxyalkylenated and ($C_6$-$C_{24}$)alkylamido ether carboxylic acids and salts thereof; at least one amphoteric and/or zwitterionic surfactant; and at least one water-insoluble carboxylic acid ester chosen from: 1) esters of a $C_3$-$C_{30}$ carboxylic acid and of a $C_1$-$C_{30}$ alcohol, with at least the acid or the alcohol being branched, and 2) esters of a $C_7$-$C_{30}$ aromatic acid whose carboxylic functional group is directly attached to the aromatic ring and of a $C_1$-$C_{30}$ alcohol; wherein the at least one water-insoluble carboxylic acid ester is present in an amount ranging from 0.5% to 10% by weight, relative to the total weight of the composition, and further wherein the sulfate or sulfonate anionic surfactant/carboxylic anionic surfactant weight ratio ranges from 2 to 12. The present disclosure also relates to a process for using the novel composition to cleanse and care for keratin materials, such as the hair, or the skin.

26 Claims, No Drawings

FOREIGN PATENT DOCUMENTS

| | | |
|---|---|---|
| JP | 2001-513534 | 9/2001 |
| JP | 2002-212592 | 7/2002 |
| JP | 2002-528478 | 9/2002 |
| JP | 2002-536311 | 10/2002 |
| JP | 2003-119500 | 4/2003 |
| JP | 2004-505145 | 2/2004 |
| WO | WO 00/72807 A2 | 12/2000 |
| WO | WO 02/055053 * | 7/2002 |

OTHER PUBLICATIONS

English language Derwent Abstract of DE 100 48 449 A1, Apr. 11, 2002.
English language Derwent Abstract of DE 100 48 450 A1, Apr. 11, 2002.
English language Derwent Abstract of DE 197 10 873 A1, Sep. 17, 1998.
English language Derwent Abstract of EP 1 034 775 A1, Sep. 13, 2000.
English language Derwent Abstract of EP 1 064 915 A1, Jan. 3, 2001.
English language Derwent Abstract of EP 1 232 739 A1, Aug. 21, 2002.
English language Derwent Abstract of EP 1 250 906 A2, Oct. 23, 2002.
English language Abstract of DE 197 10 873, dated Sep. 17, 1998.
English language Abstract of DE 101 61 885, dated Jul. 10, 2003.
English language Abstract of DE 102 61 110, dated Jul. 1, 2004.
English language Abstract of DE 39 29 973, dated Mar. 14, 1991.
English language Abstract of DE 600 00 236, dated Oct. 24, 2002.
English language Abstract of EP 1 034 775, dated Sep. 13, 2000.
Opposition to EP 1 707 240 filed by Henkel AG & Co. KGaA on Jan. 27, 2011.
Opposition to EP 1 707 240 filed by KPSS-Kao Professional Salon Services GmbH on Jan. 28, 2011.
Produktdatenblatt des Handelsprodukts Akypo® RLM 100.
Response to Notification under A.94(3) and R.71(1) filed by L'Oréal in EP 1 707 240 on Apr. 21, 2008.
*In re Merck & Co.*, 800 F.2d 1091 (Fed. Cir. 1986).
Ex parte *Gelles*, 22 U.S.P.Q.2d 1318 (B.P.A.I. 1992).
English language abstract of JP 2000-129300, May 9, 2000.
English language abstract of JP 2003-119500, Apr. 23, 2003.
English language abstract of JP 2002-212592, Jul. 31, 2002.
English language abstract of JP H10-298040, Nov. 11, 1998.
English language abstract of JP 2002-536311, Oct. 29, 2002.
English language abstract of JP H08-040845, Feb. 13, 1996.
English language abstract of JP 2000-095726, Apr. 4, 2000.

* cited by examiner

DETERGENT COSMETIC COMPOSITIONS COMPRISING THREE SURFACTANTS AND AT LEAST ONE FATTY ESTER, AND USE THEREOF

This application claims benefit of U.S. Provisional Application No. 60/669,890, filed Apr. 11, 2005, the contents of which are incorporated herein by reference. This application also claims benefit of priority under 35 U.S.C. §119 to French Patent Application No. FR 05 50808, filed Mar. 30, 2005, the contents of which are also incorporated herein by reference.

The present disclosure relates to novel cosmetic compositions with improved properties, intended for both cleaning and conditioning keratin materials such as the hair, and comprising, in a cosmetically acceptable medium, at least one sulfate or sulfonate anionic surfactant, at least one carboxylic anionic surfactant different from the preceding surfactant, at least one amphoteric and/or zwitterionic surfactant, and at least one carboxylic acid ester. The present disclosure also relates to the use of the compositions described above in a cosmetic application process.

It is common practice to use detergent compositions (such as shampoos) based essentially on standard surfactants of anionic, nonionic and/or amphoteric type, by means of an example, of anionic type, to clean and/or wash keratin materials such as the hair. These compositions are applied to wet hair and the lather generated by massaging or rubbing with the hands removes, after rinsing with water, the various types of soiling initially present on the hair or the skin.

These base compositions may have good washing power, but the intrinsic cosmetic properties associated therewith nevertheless remain fairly poor, owing for instance to the fact that the relatively aggressive nature of such a cleaning treatment can, in the long run, lead to more or less pronounced damage to the hair fiber, this damage being associated for instance with the gradual removal of the lipids or proteins contained in or on the surface of this fiber.

Thus, in order to improve the cosmetic properties of the above detergent compositions, such as those that are intended to be applied to sensitized hair (i.e. hair that has been damaged or made brittle, for example due to the chemical action of atmospheric agents and/or hair treatments such as permanent-waving, dyeing or bleaching), it is now common practice to introduce additional cosmetic agents known as conditioners into these compositions, these conditioners being intended mainly to repair or limit the harmful or undesirable effects induced by the various treatments or aggressions to which the hair fibers are subjected more or less repeatedly. These conditioners may, of course, also improve the cosmetic behavior of natural hair, following application, such as softness, gloss and disentangling properties.

With this aim, it has already been proposed to use insoluble conditioning agents. These insoluble compounds can have the drawback of being difficult to keep in uniform dispersion in the medium.

To keep them in suspension, it has already been proposed to use long-chain ester or ether derivatives (dispersants) or polysaccharides such as xanthan gum (gelling agents). However, dispersants can have crystallization problems that occasionally lead to a change (increase) in the viscosity of the compositions over time. Gelling agents can also have drawbacks, i.e., firstly, it can be difficult to develop a lather with detergent compositions containing polysaccharides (poor lather initiation) and that, secondly, the compositions may not have a smooth texture and consequently may flow in blobs, which users do not appreciate. Furthermore, these various agents do not allow transparent or clear compositions to be obtained.

Thus, there is a need in the art for compositions that do not have the drawbacks of the compositions mentioned above, while still having a detergent effect. The present disclosure proposes such novel compositions.

Accordingly, after considerable research conducted in this matter, the inventors have now found, surprisingly, that by using a combination of three types of surfactant and at least one carboxylic acid ester, it is possible to obtain stable detergent compositions with excellent cosmetic properties, for instance in terms of disentangling and smoothing out treated hair, in addition to the compositions having good working properties such as good intrinsic washing power and good latherability.

The industrial implementation of these novel compositions can be easy and the cosmetic properties of the compositions can be excellent.

The compositions obtained are stable on storage, without requiring the addition of dispersant and/or of suspension agent for the ester as disclosed herein.

In the absence of additional insoluble compounds, the compositions obtained can also be transparent. They may contain large amounts of carboxylic acid ester while at the same time maintaining good transparency and having good cosmetic properties.

The compositions in accordance with the present disclosure can have very good working properties (abundant, airy lather that develops quickly) and also very good rinseability.

The compositions in accordance with the present disclosure can give the hair, for instance after rinsing, a noteworthy treating effect that is manifested for example by the ease of disentangling, and also the provision of smoothness, softness and suppleness without any greasy sensation. The hair generally feels "natural" and cleaner.

Furthermore, these compositions can give dried hair a styling effect (i.e., can provide body and texture) making the hairstyle easier to shape, on the day of application, to the hair types that are the most difficult to control. Furthermore, this styling holds better over time.

Thus, one aspect of the present disclosure is novel detergent cosmetic compositions, wherein the compositions comprise, in a cosmetically acceptable aqueous medium, (A) at least one sulfate or sulfonate anionic surfactant; (B) at least one carboxylic anionic surfactant other than the surfactant of (A), chosen from polyoxyalkylenated ($C_6$-$C_{24}$)alkyl ether carboxylic acids, polyoxyalkylenated ($C_6$-$C_{24}$)alkylaryl ether carboxylic acids and salts thereof, and polyoxyalkylenated ($C_6$-$C_{24}$)alkylamido ether carboxylic acids and salts thereof; (C) at least one amphoteric and/or zwitterionic surfactant; and (D) at least one water-insoluble carboxylic acid ester, the esters being chosen from:

1) esters of a $C_3$-$C_{30}$ carboxylic acid and of a $C_1$-$C_{30}$ alcohol, at least the acid or the alcohol being branched, and 2) esters of a $C_7$-$C_{30}$ aromatic acid whose carboxylic functional group is directly attached to the aromatic ring and of a $C_1$-$C_{30}$ alcohol, wherein the amount of the at least one ester ranges from 0.5% to 10% by weight, relative to the total weight of the composition, and further wherein the sulfate or sulfonate anionic surfactant/ carboxylic anionic surfactant weight ratio ranges from 2 to 12.

Another aspect of the present disclosure relates to the cosmetic use of the compositions as disclosed herein for cleansing and/or removing makeup from and/or conditioning keratin materials such as the hair and the skin.

As used herein, the expression "at least one" is understood to mean one or more individual compounds, and also mixtures thereof.

(A) Sulfate or Sulfonate Surfactants

According to the present disclosure, the at least one sulfate or sulfonate anionic surfactant may be chosen from anionic surfactants comprising at least one sulfate ($-OSO_3H$ or $-OSO_3^-$) functional group and/or one sulfonate ($-SO_3H$ or $-SO_3^-$) functional group.

The at least one sulfate or sulfonate anionic surfactant that may be used, in the context of the present disclosure can be salts (such as alkali metal salts, for example of sodium, ammonium salts, amine salts, amino alcohol salts or magnesium salts) of alkyl sulfates, alkylamido sulfates, alkyl ether sulfates, alkylamido ether sulfates, alkylaryl ether sulfates, alkyl ether sulfosuccinates, acyl isethionates, methyl acyl taurates; the alkyl or acyl radical of all these various compounds may contain, for example, from 8 to 24 carbon atoms, and the aryl radical may contain, for instance, a phenyl or benzyl group.

The average number of ethylene oxide or propylene oxide groups may, for example, range from 2 to 50 and further, for example, from 2 to 10.

Among these anionic surfactants, mention may be made of, for instance, $C_8$-$C_{14}$, such as the $C_{12}$-$C_{14}$ alkyl ether sulfate salts. For example, these salts may comprise from 2 to 5 ethylene oxide groups.

As disclosed herein, the at least one anionic surfactant may be chosen from sodium, triethanolamine, magnesium or ammonium ($C_{12}$-$C_{14}$)alkyl sulfates, sodium, ammonium or magnesium ($C_{12}$-$C_{14}$)alkyl ether sulfates oxyethylenated with 2.2 mol of ethylene oxide, sodium cocoylisethionate and methylacyl taurates, for example.

The at least one sulfate or sulfonate anionic surfactant can be present in an amount ranging from 1.5% to 50% by weight, such as from 2% to 25% by weight, for instance ranging from 5% to 25% by weight, for example ranging from 8% to 20% by weight and further, for example, from 10% to 16% by weight, relative to the total weight of the composition.

(B) Carboxylic Anionic Surfactants

According to the present disclosure, the carboxylic anionic surfactants include but are not limited to anionic surfactants comprising at least one carboxylic function ($-COOH$) optionally in salt form ($-COO^-$).

As disclosed herein, the at least one anionic surfactant of carboxylic type, other than the surfactants (A), for instance, can comprise no sulfate or sulfonate functional groups and may be chosen for example from polyoxyalkylenated ($C_6$-$C_{24}$)alkyl ether carboxylic acids, polyoxyalkylenated ($C_6$-$C_{24}$)alkylaryl ether carboxylic acids and salts thereof, polyoxyalkylenated ($C_6$-$C_{24}$)alkylamido ether carboxylic acids and salts thereof, such as for example, those containing from 2 to 50 alkylene oxide groups, for instance ethylene oxide, such as the compounds sold by the company Kao under the name Akypo.

As previously discussed above in the definition of "at least one," mixtures of these surfactants may also be used.

The salts may be chosen for instance from alkali metal salts, for example of sodium, ammonium salts, amine salts, salts of amino alcohols such as triethanolamine or monoethanolamine, and magnesium salts.

Polyoxyalkylenated ($C_6$-$C_{24}$)alkyl ether carboxylic acids and salts thereof, polyoxyalkylenated ($C_6$-$C_{24}$)alkylamido ether carboxylic acids and for instance those containing from 2 to 15 alkylene oxide groups, and salts thereof, and mixtures thereof may also be used.

As disclosed herein, according to at least one embodiment, the at least one anionic surfactant of the polyoxyalkylenated carboxylic ether acid or salt type include, for instance, those of formula (1):

$$R_1-(OC_2H_4)_n-OCH_2COOA \quad (1)$$

in which:

$R_1$ is chosen from linear and branched $C_8$-$C_{22}$ alkyl and alkenyl radicals, ($C_8$-$C_9$)alkylphenyl radicals, $R_2CONH-CH_2-CH_2-$ radicals, wherein R2 is chosen from linear and branched $C_{11}$-$C_{21}$ alkyl and alkenyl radicals, and n is an integer or decimal number (average value) that may range from 2 to 24, for example, from 2 to 10, the alkyl radical containing between 6 and 20 carbon atoms such as from 8 to 18 carbon atoms, and aryl is, for example, a phenyl, and further, for example, A is an entity chosen from H, ammonium, Na, K, Li, Mg or a monoethanolamine or triethanolamine residue. Mixtures of compounds of formula (1) may also be used, for example mixtures in which the groups $R_1$ are different.

According to one embodiment as disclosed herein, the oxyalkylenated ether carboxylic acids or salts thereof may be chosen from those of formula (1) in which $R_1$ is chosen from ($C_{12}$-$C_{14}$)alkyl, cocoyl and oleyl radicals; and nonylphenyl and octylphenyl radicals, A is chosen from hydrogen and sodium atoms, and n ranges from 2 to 20, such as from 2 to 10.

According to another embodiment of the present disclosure, the compounds of formula (1) may be used in which R is a ($C_{12}$)alkyl radical, A is a hydrogen or sodium atom and n ranges from 2 to 10.

The commercial products that may be used, for example, include but are not limited to the products sold by the company Chem Y under the names:

Akypo® NP 70 (R=nonylphenyl, n=7, p=0, A=H);
Akypo® NP 40 (R=nonylphenyl, n=4, p=0, A=H);
Akypo® OP 40 (R=octylphenyl, n=4, p=0, A=H);
Akypo® OP 80 (R=octylphenyl, n=8, p=0, A=H);
Akypo® OP 190 (R=octylphenyl, n=19, p=0, A=H);
Akypo® RLM 38 (R=($C_{12}$-$C_{14}$)alkyl, n=3.8, p=0, A=H);
Akypo® RLM 38 NV (R=($C_{12}$-$C_{14}$)alkyl, n=4, p=0, A=Na);
Akypo® RLM 45 (R=($C_{12}$-$C_{14}$)alkyl, n=4.5, p=0, A=H);
Akypo® RLM 45 NV (R=($C_{12}$-$C_{14}$)alkyl, n=4.5, p=0, A=Na);
Akypo® RLM 100 (R=($C_{12}$-$C_{14}$)alkyl, n=10, p=0, A=H);
Akypo® RLM 100 NV (R=($C_{12}$-$C_{14}$)alkyl, n=10, p=0, A=Na);
Akypo® RLM 130 (R=($C_{12}$-$C_{14}$)alkyl, n=13, p=0, A=H);
Akypo® RLM 160 NV (R=($C_{12}$-$C_{14}$)alkyl, n=16, p=0, A=Na);

or by the company Sandoz under the names:
Sandopan DTC-Acid (R=($C_{13}$)alkyl, n=6, p=0, A=H);
Sandopan DTC (R=($C_{13}$)alkyl, n=6, p=0, A=Na);
Sandopan LS 24 (R=($C_{12}$-$C_{14}$)alkyl, n=12, p=0, A=Na);
Sandopan JA 36 (R=($C_{13}$)alkyl, n=18, p=0, A=H), and for further non-limiting example the products sold under the following names:
Akypo® RLM 45;
Akypo® RLM 100;
Akypo® RLM 38.

The at least one carboxylic anionic surfactant other than the surfactants of (A) can be present in an amount ranging from 0.5% to 15% by weight, such as from 1% to 10% by weight, for example from 1% to 5% by weight and further for example from 1.5% to 3% by weight, relative to the total weight of the composition.

(C) Amphoteric and/or Zwitterionic Surfactant(s):

The at least one amphoteric and/or zwitterionic surfactant, whose nature is not a critical feature in the context of the present disclosure may be chosen from, but not limited to, aliphatic secondary and tertiary amine derivatives in which the aliphatic radical is chosen from linear and branched chains containing 8 to 22 carbon atoms and containing at least one water-soluble anionic group (for example carboxylate, sulfonate, sulfate, phosphate or phosphonate); non-limiting mention may also be made of ($C_8$-$C_{20}$)alkylbetaines, sulfobetaines, ($C_8$-$C_{20}$)alkylamido($C_1$-$C_6$)alkylbetaines and ($C_8$-$C_{20}$)alkylamido($C_1$-$C_6$)alkylsulfobetaines.

The amine derivatives as disclosed herein, include but are not limited to the products as described in U.S. Pat. Nos. 2,528,378, and 2,781,354 and chosen from those of formulae (2) and (3):

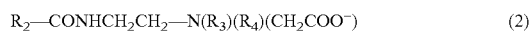

in which: $R_2$ is chosen from C6-C24 acyl radicals, for example a radical present in hydrolysed coconut oil, an octoyl, decoyl or dodecanoyl radical, and mixtures thereof, $R_3$ is a β-hydroxyethyl group and $R_4$ is a carboxymethyl group; and

in which:
(B) is chosen from —$CH_2CH_2OX'$ radicals, (C') is chosen from —$(CH_2)_n$—Y' radicals, with z=1 or 2,
X' is chosen from —$CH_2CH_2$—COOH groups and a hydrogen atom,
Y' is chosen from —COOH and —$CH_2$—CHOH—$SO_3H$ radicals,
$R'_2CO$ is a C6-C24 acyl radical, for example a radical present in hydrolysed coconut oil or linseed oil, or an octoyl, decoyl or dodecanoyl, stearoyl, isostearoyl or oleoyl radical, and mixtures thereof.

These compounds are classified in the CTFA Dictionary, 5th Edition (1993) under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium capryloamphodipropionate, lauroamphodipropionic acid, and cocoamphodipropionic acid.

By way of non-limiting example, disodium cocoamphodiacetate may be mentioned, sold under the trade name Miranol® C2M concentrate by the company Rhodia Chimie.

According to at least one embodiment of the present disclosure, amphoteric surfactants belonging to the betaine group such as alkylbetaines may be used, such as, the cocoylbetaine sold under the name Dehyton AB 30 as an aqueous solution containing 30% AM by the company Henkel, or alkylamidobetaines, and further, for example, cocamidopropylbetaine, such as Tegobetaine® F50 sold by the company Goldschmidt.

The at least one amphoteric and/or zwitterionic surfactant can be present in an amount ranging from 0.1% to 20% by weight, such as ranging from 1% to 15% by weight and for example, such as ranging from 1.5% to 5% by weight, relative to the total weight of the composition.

The minimum amount of all three surfactants is the amount that is sufficient to give the final composition satisfactory latherability and/or satisfactory detergent power. Excessive amounts of washing base do not really give any further benefits.

The minimum amount of all three surfactants is the amount that is sufficient to give the final composition satisfactory latherability and/or satisfactory detergent power. Excessive amounts of washing base do not really give any further benefits.

Thus, according to the present disclosure, the total amount of surfactants may range from 4% to 50% by weight, for instance from 6% to 35% by weight, such as from 8% to 25% by weight and further still from 14% to 20% by weight, relative to the total weight of the final composition.

The weight ratio of the at least one sulfate or sulfonate anionic surfactant to the at least one amphoteric and/or zwitterionic surfactant may range from 2 to 12, for instance from 4 to 10 and further, for example, from 5 to 8.

The weight ratio of the at least one sulfate or sulfonate anionic surfactant to the at least one carboxylic anionic surfactant may range from 4 to 10, for instance from 5 to 8.

The weight ratio of the at least one carboxylic anionic surfactant to the at least one amphoteric and/or zwitterionic surfactant may range from 0.3 to 3, for instance from 0.5 to 1.5.

(D) Carboxylic Acid Esters:

The water-insoluble carboxylic acid esters according to the present disclosure are insoluble in water at a concentration of greater than or equal to 0.1% by weight in water at 25° C, i.e. they do not form an isotropic solution that is transparent to the naked eye under these conditions.

The esters that may be used in the present disclosure may be monomeric, for example. The esters may also be nonionic, non-silicone esters.

The water-insoluble carboxylic acid esters according to the present disclosure may contain hydroxyl groups.

The total carbon number of the esters of the present disclosure may, for instance, range from 12 to 50, such as from 16 to 40 and further, for example, from 16 to 30.

According to the present disclosure, the esters used may be, for example, liquid at room temperature (25° C.) and at atmospheric pressure (1 atm).

The at least one carboxylic ester as disclosed herein may be chosen from:
1) esters of a $C_3$-$C_{30}$ carboxylic acid and of a $C_1$-$C_{30}$ alcohol, at least the acid or the alcohol being branched or containing, at least one carbon-carbon double bond, and
2) esters of a $C_7$-$C_{30}$ aromatic acid whose carboxylic functional group is directly linked to the aromatic ring, and of a $C_1$-$C_{30}$ alcohol.

In one embodiment of the present disclosure, the esters of a $C_3$-$C_{30}$ carboxylic acid and of a $C_1$-$C_{30}$ alcohol, at least the acid or the alcohol being branched or unsaturated, may be chosen from esters of a $C_6$-$C_{24}$ carboxylic acid and of a $C_3$-$C_{20}$ alcohol.

The esters according to the present disclosure may be chosen from, for example:
esters of a branched carboxylic acid containing from 4 to 6 carbon atoms and of an alcohol containing from 8 to 26 carbon atoms,
esters of a linear carboxylic acid containing from 12 to 26 carbon atoms and of a branched alcohol containing from 3 to 12 carbon atoms,
esters of a linear carboxylic acid containing from 2 to 12 carbon atoms and of a branched alcohol containing from 8 to 26 carbon atoms, esters of a branched carboxylic acid containing from 8 to 26, for instance from 8 to 12 carbon atoms, and of a branched alcohol containing from 8 to 26, for example from 8 to 12 carbon atoms.

Non-limiting mention may be made of octyldodecyl behenate; isocetyl behenate; isocetyl lactate; isostearyl lactate; isostearyl octanoate; isocetyl octanoate; isocetyl isostearate; isocetyl laurate; isocetyl stearate; isodecyl octanoate; isodecyl oleate; isononyl isononanoate; isostearyl palmitate; myristyl isostearate; octyl isononanoate; 2-ethylhexyl isononate; octyl isostearate; octyldodecyl erucate; isopropyl palmitate, 2-ethylhexyl palmitate, 2-octyldecyl palmitate, branched alkyl myristates such as isopropyl, tert-butyl or 2-octyidodecyl myristate, hexyl isostearate, butyl isostearate, isobutyl stearate; 2-hexyldecyl laurate.

As disclosed herein, for instance, the acid and the alcohol of the ester may be saturated.

Liquid esters of a branched carboxylic acid containing from 4 to 6 carbon atoms and of an alcohol containing from 8 to 26 carbon atoms may also be used.

According to at least one embodiment disclosed herein, the branched liquid esters according to the present disclosure may be chosen from those of formula (I'):

$$R_1COOR_2 \quad (I')$$

in which:

$R_1$ is chosen from linear and branched, optionally mono- or polyhydroxylated hydrocarbon-based radicals containing from 3 to 5 carbon atoms, $R_2$ is chosen from linear and branched, optionally mono- or polyhydroxylated hydrocarbon-based radicals containing from 12 to 26 carbon atoms, for instance containing from 16 to 22 carbon atoms.

In one embodiment of the present disclosure, $R_1$ is chosen from branched alkyl radicals containing from 3 to 5 carbon atoms, for example a tert-butyl radical.

In another embodiment, $R_2$ is chosen from saturated or unsaturated alkyl radicals containing from 12 to 26 carbon atoms, for example a branched radical, such as tridecyl, isocetyl, isostearyl, octyldodecyl and isoarachidyl radicals.

The branched liquid esters that may be used include but are not limited to isostearyl neopentanoate (formula (I) in which $R_1$=tert-butyl and $R_2$=isostearyl), tridecyl neopentanoate, isocetyl neopentanoate and isoarachidyl neopentanoate.

The esters of a $C_7$-$C_{30}$ aromatic acid and of a $C_1$-$C_{30}$ alcohol, include but are not limited to esters of a $C_7$-$C_{17}$ aromatic acid and of a $C_1$-$C_{20}$ alcohol. For example, these esters may be chosen from $C_{12}$-$C_{15}$ alkyl benzoaes, isostearyl benzoate, octyldodecyl benzoate, behenyl benzoate, and 2-ethylhexyl benzoate.

As disclosed herein, the carboxylic acid esters may be chosen, for instance, from:
isostearyl lactate; lauryl lactate; isostearyl octanoate; isocetyl octanoate; isodecyl octanoate;
isononyl isononanoate; octyl isononanoate, 2-ethylhexl isononate; octyldodecyl erucate, isopropyl palmitate, 2-ethylhexyl palmitate,
isopropyl myristate, isobutyl stearate; diisopropyl sebacate; diisoprolyl adipate; triisopropyl citrate;
isostearyl neopentanoate, and tridecyl neopentanoate.

The esters as disclosed herein may be chosen from, but are not limited to, isopropyl palmitate, 2-ethylhexyl palmitate, isopropyl or tert-butyl myristate, butyl isostearate, isobutyl stearate; isononyl isononanoate and isostearyl neopentanoate.

The esters according to the present disclosure also include, but are not limited to monoesters of a carboxylic acid and of a monoalcohol.

The at least one carboxylic acid ester may be present in the compositions in accordance with the present disclosure in an amount ranging from 0.5% to 5% by weight, such as ranging from 0.8% to 3% by weight, relative to the total weight of the composition.

According to at least one embodiment of the present disclosure, the compositions may also comprise at least one water-soluble salt and/or a mono- or polyhydroxylated water-soluble alcohol. The water-soluble salts according to the disclosure include but are not limited to salts of monovalent or divalent metals and of a mineral or organic acid.

Non-limiting mention may be made, for example, of sodium chloride, potassium chloride, calcium chloride, magnesium sulfate, sodium citrate and the sodium salts of phosphoric acid. For example, in one embodiment, sodium chloride may be used.

The detergent compositions according to the present disclosure may have a final pH ranging from 3 to 8. For instance, the final pH may range from 4 to 7.5. The final pH may be adjusted to the desired value conventionally by adding a base (organic or mineral) to the composition, for example sodium hydroxide, aqueous ammonia or a primary, secondary or tertiary (poly)amine, for instance monoethanolamine, diethanolamine, triethanolamine, isopropanolamine or 1,3-propanediamine, or alternatively by adding a mineral or organic acid, such as citric acid or hydrochloric acid.

The cosmetically acceptable aqueous medium may consist solely of water or comprise a mixture of water and at least one cosmetically acceptable solvent, such as a $C_1$-$C_4$ lower alcohol, for instance ethanol, isopropanol, tert-butanol or n-butanol; alkylene glycols, for instance propylene glycol, hexylene glycol or glycerol.

The composition according to at least one embodiment of the present disclosure may comprise at least 30% by weight of water, such as from 50% to 90% by weight of water, and further for example from 70% to 85% by weight of water, relative to the total weight of the composition.

For example, the composition as disclosed herein may comprise less than 20% by weight of fatty phase, relative to the total weight of the composition.

The fatty phase of the compositions as disclosed herein may comprise all the fatty substances of the composition that are insoluble in water at room temperature, such as, for example, fatty esters, plant, mineral or synthetic oils, fatty alcohols, fatty acids, fatty amides, waxes and silicones. For instance, the fatty phase may be present in an amount ranging from 0.1% to 15% by weight, for example from 0.5% to 10% by weight, and even further, for example, from 0.5% to 8% by weight, relative to the total weight of the composition.

The compositions in accordance with the present disclosure may comprise, in addition to the combination defined above, at least one viscosity regulator such as thickeners. Non-limiting mention may be made, for instance, of scleroglucans, xanthan gums, fatty acid alkanolamides, alkyl ether carboxylic acid alkanolamides optionally oxyethylenated with up to 5 mol of ethylene oxide, such as the product sold under the name Aminol A15 by the company Chem Y, crosslinked polyacrylic acids and crosslinked acrylic acid/$C_{10}$-$C_{30}$ alkyl acrylate copolymers. These viscosity regulators may be used in the compositions according to the present disclosure in an amount less than or equal to 10% by weight, relative to the total weight of the composition.

The compositions in accordance with the present disclosure may also comprise less than or equal to 5% by weight of at least one nacreous agent and/or opacifiers that are well known in the state of the art, for instance fatty alcohols, sodium palmitate or magnesium palmitate, sodium or magnesium stearate or hydroxystearate, fatty alcohols, fatty-chain acyl derivatives such as ethylene glycol or polyethylene glycol distearates, and fatty-chain ethers, for instance distearyl ether or 1-(hexadecyloxy)-2-octadecanol.

The compositions in accordance with the present disclosure may also optionally comprise other agents which have the effect of improving the cosmetic properties of the hair or the skin without, however, impairing the stability of the compositions. Non-limiting mention may be made in this respect of cationic surfactants, anionic, nonionic, cationic or amphoteric polymers, proteins, protein hydrolysates, ceramides, pseudoceramides, plant oils, fatty acids, for example containing linear or branched $C_{16}$-$C_{40}$ chains such as 18-methyleicosanoic acid, hydroxy acids, vitamins, provitamins such as panthenol, volatile or non-volatile silicones, which are soluble or insoluble in the medium, UV-screening agents, moisturizers, antidandruff or anti-seborrhoeic agents, hair-loss counteractants and free-radical scavengers, and mixtures thereof.

According to at least one embodiment of the present disclosure, the compositions according to the disclosure may also comprise at least one cationic polymer.

The at least one cationic polymer that may be used in accordance with the present disclosure may be chosen from any of those already known per se as improving the cosmetic properties of hair treated with detergent compositions, for example those described in the European Patent Application No. EP-A-0 337 354, and French Patent Application Nos. FR-A-2 270 846, FR-A-2 383 660, FR-A-2 598 611, FR-A-2 470 596 and FR-A-2 519 863.

For the purposes of the present disclosure, the expression "cationic polymer" is generally understood to mean any polymer containing cationic groups and/or groups that can be ionized into cationic groups.

The cationic polymers that may be used according to the present disclosure may, for example, have a cationic charge density of greater than or equal to 0.2 meq./g, such as between 0.2 and 8.5 meq./g.

The cationic polymers that may be used in the context of the present disclosure, include but are not limited to quaternary cellulose ether derivatives such as the products sold under the name JR 400 by the company Union Carbide Corporation, cyclopolymers, for instance diallyldimethylammonium salt homopolymers and copolymers of a diallyldimethylammonium salt and of acrylamide, for example the chlorides, sold under the names Merquat 100, Merquat 550 and Merquat S by the company Merck, cationic polysaccharides and further, for instance, guar gums modified with 2,3-epoxypropyltrimethylammonium chloride, sold, for example, under the name Jaguar C13S by the company Meyhall, optionally crosslinked homopolymers and copolymers of (meth)acryloyloxyethyltrimethylammonium salt, sold by the company Allied Colloids as a 50% solution in mineral oil under the trade names Salcare SC92 (crosslinked copolymer of methacryloyloxyethyltrimethylammonium chloride and of acrylamide) and Salcare SC95 (crosslinked homopolymer of methacryloyloxyethyltrimethylammonium chloride), quaternary copolymers of vinylpyrrolidone and of a vinylimidazole salt such as the products sold by BASF under the names Luviquat FC 370, Luviquat FC 550, Luviquat FC 905 and Luviquat HM-552.

According to at least one embodiment of the present disclosure, it is also possible to use polymers that comprise repeating units of formula (I):

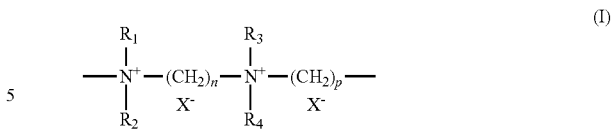

in which $R_1$, $R_2$, $R_3$ and $R_4$, which may be identical or different, are chosen from alkyl and hydroxyalkyl radicals containing from 1 to 4 carbon atoms, n and p are integers ranging from 2 to 20 approximately, and $X^-$ is an anion derived from a mineral or organic acid.

For example, a compound of formula (I) that may be used is the compound for which $R_1$, $R_2$, $R_3$ and $R_4$ represent a methyl radical and n=3, p=6 and X=Cl, known as Hexadimethrine chloride according to the INCI nomenclature (CTFA).

According to the present disclosure, the at least one cationic polymer may be present in an amount ranging from 0.001% to 10% by weight, such as from 0.0005% to 5% by weight and further, for example, from 0.01% to 3% by weight, relative to the total weight of the final composition.

The compositions according to the present disclosure may also comprise at least one foam synergists such as $C_{10}$-$C_{18}$ 1,2-alkanediols or $C_{10}$-$C_{18}$ fatty alkanolamides derived from monoethanolamine or from diethanolamine.

Needless to say, a person skilled in the art will take care to select this or these optional additional compound(s) and/or the amounts thereof such that the solubility of the carboxylic acid esters according to the present disclosure, the stability of the composition and the cosmetic properties intrinsically associated with the composition in accordance with the present disclosure are not, or are not substantially, adversely affected by the envisaged addition(s). The addition of certain compounds such as nacreous agents may make the composition non-transparent.

The transparency may be measured by measuring the transmittance at 700 nm via a spectrometer (for example a Lambda 14 spectrometer from Perkin-Elmer or a UV21 01 PC spectrometer from Shimadzu). The transparent compositions have a transmittance of greater than or equal to 94%, for example from 96% to 100%.

The latherability of the compositions according to the present disclosure, are characterized by a foam height that may be greater than or equal to 75 mm, for example greater than or equal to 100 mm, measured according to the amended Ross-Miles method (NF T 73-404/ISO696).

The amendments to the method are the following:

The measurement is performed at a temperature of 22° C. with osmosed water. The concentration of the solution is 2 g/l. The height of the drop is 1 m. The amount of composition that is dropped is 200 ml. These 200 ml of composition fall into a measuring cylinder with a diameter of 50 mm and containing 50 ml of the test composition. The measurement is taken 5 minutes after stopping the flow of the composition.

These compositions may be in the form of more or less thickened liquids, creams or gels, and they are mainly suitable for washing and caring for keratin materials, for example the hair and the skin, such as the hair.

Another aspect of the present disclosure includes a process for washing and conditioning keratin materials, for example, such as the hair, which comprises applying an effective amount of the composition as disclosed herein to the wet keratin materials, and then rinsing away the composition with water after an optional leave-in time.

The compositions according to the present disclosure may be used as shampoos for washing and conditioning the hair, and they are applied, in this case, to wet hair in amounts that are suitable to wash them, and the lather generated by massaging or rubbing with the hands is then removed after an optional leave-in time, by rinsing with water, the operation possibly being repeated at least one time.

The compositions in accordance with the present disclosure may also be used as shower gels for washing and conditioning the hair and/or the skin, in which case they are applied to the wet skin and/or hair and are rinsed off after application.

The contents of the documents mentioned previously are hereby incorporated by reference into the present patent application.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in its respective testing measurement.

The examples that follow are intended to illustrate the present disclosure without, however, being limiting in nature.

EXAMPLES

Examples 1 and 2

The shampoo compositions below in accordance with the present disclosure were prepared:

|  | 1 | 2 |
|---|---|---|
| Sodium lauryl ether sulfate (70/30 C12/C14) containing 2.2 mol of ethylene oxide, as an aqueous solution containing 70% AM | 14.2 g AM | 14.2 g AM |
| Cocoylbetaine containing 30% AM (Dehyton AB 30 from Cognis) | 1.9 g AM | 1.9 g AM |
| Lauryl ether carboxylic acid (Akypo RLM 45 CA from Kao) | 1.8 g AM | 1.8 g AM |
| Isopropyl myristate | 2 g | — |
| Isostearyl neopentanoate | — | 1 g |
| Cationic cellulose (JR400 from Amerchol) | 0.3 g | 0.3 g |
| Coconut acid monoisopropanolamide | 3.3 g | 3.3 g |
| Fragrance, preserving agent | qs | qs |
| Hydrochloric acid qs pH | 5-5.6 | 5-5.6 |
| Demineralized water qs | 100 g | 100 g |
| Transmittance | >94% | >94% |

The compositions according to the present disclosure were transparent and stable.

When the compositions were applied to wet hair, the lather developed quickly, was abundant and rinsed out easily.

Hair treated with these compositions disentangled easily and was smooth from the root to the end. It felt clean and had good body.

Example 3

The shampoo composition in accordance with the present disclosure was prepared.

|  | 3 |
|---|---|
| Sodium lauryl ether sulfate (70/30 C12/C14) containing 2.2 mol of ethylene oxide, as an aqueous solution containing 70% AM | 10 g AM |
| Sodium methylcocoyltaurate at 30% in water (Hostapon LT-SF from Clariant) | 3 g AM |
| Triethanolamine cocoylglutamate at 30% in water (Amisoft CT 12 from Ajinomoto) | 2 g AM |
| Disodium cocodiamphodiacetate at 39% active material (Miranol C2M CONC from Rhodia) | 3 g AM |
| Lauryl ether carboxylic acid (Akypo RLM 45 CA from Kao) | 1.8 g AM |
| Isopropyl myristate | 2 g |
| Cationic cellulose (JR400 from Amerchol) | 0.3 g |
| Coconut acid monoisopropanolamide | 3.3 g |
| Fragrance, preserving agent | qs |
| Hydrochloric acid qs pH | 5-5.6 |
| Demineralized water qs | 100 g |
| Transmittance | >94% |

Results similar to those of Examples 1 and 2 were obtained.

Examples 4 and 5

The shampoo compositions below in accordance with the present disclosure were prepared:

|  | 4 | 5 |
|---|---|---|
| Sodium lauryl ether sulfate (70/30 C12/C14) containing 2.2 mol of ethylene oxide, as an aqueous solution containing 70% AM | 12.6 g AM | 12.6 g AM |
| Cocoylbetaine containing 30% AM (Dehyton AB 30 from Cognis) | 2.07 g AM | 2.07 g AM |
| Lauryl ether carboxylic acid containing 10 mol of ethylene oxide (Akypo RLM 100 from Kao) | 1.8 g AM | 3.6 g AM |
| Isostearyl neopentanoate | 1 g | 1 g |
| Cationic cellulose (JR400 from Amerchol) | 0.27 g | 0.27 g |
| Coconut acid monoisopropanolamide | 2.94 g | 2.94 g |
| Fragrance, preserving agent | qs | qs |
| Hydrochloric acid qs pH | 5-5.6 | 5-5.6 |
| Demineralized water qs | 100 g | 100 g |
| Transmittance | >94% | >94% |

Results similar to those of Examples 1 and 2 were obtained.

Examples 6 and 7

The shampoo compositions below in accordance with the present disclosure were prepared:

|  | 6 | 7 |
|---|---|---|
| Sodium lauryl ether sulfate (70/30 C12/C14) containing 2.2 mol of ethylene oxide, as an aqueous solution | 12.6 g AM | 14.2 g AM |

-continued

|  | 6 | 7 |
|---|---|---|
| containing 70% AM |  |  |
| Cocoylamidopropylbetaine containing 35% AM (Velvetex BK 35) | 2.07 g AM | — |
| Cocoylbetaine containing 30% AM (Dehyton AB 30 from Cognis) |  | 1.9 g AM |
| Isostearyl neopentanoate | 1 g |  |
| Isopropyl myristate |  | 1 g |
| Cationic cellulose (JR400 from Amerchol) | 0.27 g | 0.27 g |
| Coconut acid monoisopropanolamide | 2.94 g | 3.3 g |
| Fragrance, preserving agent | qs | qs |
| Hydrochloric acid qs pH | 5-5.6 | 5-5.6 |
| Demineralized water qs | 100 g | 100 g |
| Transmittance | >94% | >94% |

Results similar to those of Examples 1 and 2 were obtained.

Example 8

The shampoo composition below in accordance with the present disclosure was prepared:

|  | 8 |
|---|---|
| Ammonium lauryl sulfate (70/30 C12/C14) as an aqueous solution containing 70% AM | 12.6 g AM |
| Cocoylbetaine containing 30% AM (Dehyton AB 30) | 2.07 g AM |
| Lauryl ether carboxylic acid (Akypo RLM 45 CA from Kao) | 1.8 g AM |
| Isostearyl neopentanoate | 1 g |
| Cationic cellulose (JR400 from Amerchol) | 0.27 g |
| Coconut acid monoisopropanolamide | 2.94 g |
| Fragrance, preserving agent | qs |
| Hydrochloric acid qs pH | 5-5.6 |
| Demineralized water qs | 100 g |
| Transmittance | >94% |

Results similar to those of Examples 1 and 2 were obtained.

Example 9

The shampoo composition below in accordance with the present disclosure was prepared:

|  | 9 |
|---|---|
| Sodium lauryl ether sulfate (70/30 C12/C14) containing 2.2 mol of ethylene oxide, as an aqueous solution containing 70% AM | 12.6 g AM |
| Cocoylbetaine containing 30% AM (Dehyton AB 30 from Cognis) | 4.14 g AM |
| Lauryl ether carboxylic acid (Akypo RLM 45 CA from Kao) | 1.8 g AM |
| Isopropyl myristate | 1 g |
| Cationic cellulose (JR400 from Amerchol) | 0.27 g |
| Coconut acid monoisopropanolamide | 2.94 g |
| Fragrance, preserving agent | qs |
| Hydrochloric acid qs pH | 5-5.6 |
| Demineralized water qs | 100 g |
| Transmittance | >94% |

Results similar to those of Examples 1 and 2 were obtained.

What is claimed is:

1. A detergent cosmetic composition, comprising, in a cosmetically acceptable aqueous medium:
(A) at least one sulfate or sulfonate anionic surfactant;
(B) at least one carboxylic anionic surfactant other than the surfactant of (A), chosen from polyoxyalkylenated ($C_6$-$C_{24}$)alkyl ether carboxylic acids, polyoxyalkylenated ($C_6$-$C_{24}$)alkylaryl ether carboxylic acids and salts thereof, and polyoxyalkylenated ($C_6$-$C_{24}$)alkylamido ether carboxylic acids and salts thereof;
(C) at least one amphoteric and/or zwitterionic surfactant, and
(D) at least one water-insoluble carboxylic acid ester chosen from esters of a $C_3$-$C_{30}$ carboxylic acid and of a $C_1$-$C_{30}$ alcohol, with at least the acid or the alcohol being branched, wherein the total carbon number of the at least one water-insoluble carboxylic acid ester ranges from 12 to 50;
wherein the at least one sulfate or sulfonate anionic surfactant is present in an amount ranging from 5% to 25% by weight, relative to the total weight of the composition,
wherein the at least one carboxylic anionic surfactant is present in an amount ranging from 0.5% to 15% by weight, relative to the total weight of the composition,
wherein the at least one amphoteric and/or zwitterionic surfactant is present in an amount ranging from 0.1% to 20% by weight, relative to the total weight of the composition,
wherein the at least one water-insoluble carboxylic acid ester is present in an amount ranging from 0.5% to 10% by weight, relative to the total weight of the composition, and
further wherein the weight ratio of the at least one sulfate or sulfonate anionic surfactant to the at least one carboxylic anionic surfactant ranges from 4 to 10.

2. The detergent cosmetic composition according to claim 1, wherein the total amount of surfactant ranges from 6% to 50% by weight, relative to the total weight of the composition.

3. The detergent cosmetic composition according to claim 2, wherein the total amount of surfactant ranges from 14% to 20% by weight, relative to the total weight of the composition.

4. The detergent cosmetic composition according to claim 1, wherein the at least one sulfate or sulfonate anionic surfactant is present in an amount ranging from 10% to 16% by weight, relative to the total weight of the composition.

5. The detergent cosmetic composition according to claim 1, wherein the at least one amphoteric and/or zwitterionic surfactant is present in an amount ranging from 1.5% to 5% by weight, relative to the total weight of the composition.

6. The detergent cosmetic composition according to claim 1, wherein the at least one carboxylic anionic surfactant is present in an amount ranging from 1.5% to 5% by weight, relative to the total weight of the composition.

7. The detergent cosmetic composition according to claim 1, wherein the weight ratio of the at least one sulfate or sulfonate anionic surfactant to the at least one amphoteric and/or zwitterionic surfactant ranges from 2 to 12.

8. The detergent cosmetic composition according to claim 7, wherein the weight ratio of the at least one sulfate or sulfonate anionic surfactant to the at least one amphoteric and/or zwitterionic surfactant ranges from 4 to 10.

9. The detergent cosmetic composition according to claim 1, wherein the weight ratio of the at least one carboxylic anionic surfactant to the at least one amphoteric and/or zwitterionic surfactant ranges from 0.3 to 3.

10. The detergent cosmetic composition according to claim 9, wherein the weight ratio of the at least one carboxylic anionic surfactant to the at least one amphoteric and/or zwitterionic surfactant ranges from 0.5 to 1.5.

11. The detergent cosmetic composition according to claim 1, wherein the at least one water-insoluble carboxylic acid ester is a liquid ester chosen from:
  esters of a branched carboxylic acid containing from 4 to 6 carbon atoms and of an alcohol containing from 8 to 26 carbon atoms,
  esters of a linear carboxylic acid containing from 12 to 26 carbon atoms and of a branched alcohol containing from 3 to 12 carbon atoms,
  esters of a linear carboxylic acid containing from 3 to 12 carbon atoms and of a branched alcohol containing from 8 to 26 carbon atoms,
  esters of a branched carboxylic acid containing from 8 to 26 carbon atoms and of a branched alcohol containing from 8 to 26 carbon atoms.

12. The detergent cosmetic composition according to claim 1, wherein the at least one water-insoluble carboxylic acid ester is chosen from: isostearyl lactate; isostearyl octanoate; isocetyl octanoate; isodecyl octanoate; isononyl isononanoate; octyl isononanoate; 2-ethylhexyl isononate; isopropyl palmitate, 2-ethylhexyl palmitate, isopropyl myristate, tert-butyl myristate, isobutyl stearate; diisopropyl sebacate; diisopropyl adipate; triisopropyl citrate; isostearyl neopentanoate, and tridecyl neopentanoate.

13. The detergent cosmetic composition according to claim 12, wherein the at least one water-insoluble carboxylic acid ester is chosen from isopropyl palmitate, 2-ethylhexyl palmitate, isopropyl or tert-butyl myristate, butyl isostearate, isobutyl stearate, isononyl isononanoate and isostearyl neopentanoate.

14. The detergent cosmetic composition according to claim 13, wherein the at least one water-insoluble carboxylic acid ester is chosen from isopropyl palmitate, isopropyl myristate, tert-butyl myristate, isononyl isononanoate and isostearyl neopentanoate.

15. The detergent cosmetic composition according to claim 1, wherein the at least one water-insoluble carboxylic acid ester is present in an amount ranging from 0.5% to 5% by weight, relative to the total weight of the composition.

16. The detergent cosmetic composition according to claim 15, wherein the at least one water-insoluble carboxylic acid ester is present in an amount ranging from 0.8% to 3% by weight, relative to the total weight of the composition.

17. The detergent cosmetic composition according to claim 1, further comprising at least one cationic polymer.

18. The detergent cosmetic composition according to claim 17, wherein the at least one cationic polymer is chosen from quaternary cellulose ether compounds, diallyldimethylammonium salt homopolymers and copolymers of a diallyldimethylammonium salt and of acrylamide, cationic polysaccharides, and quaternary copolymers of vinylpyrrolidone and of a vinylimidazole salt.

19. The detergent cosmetic composition according to claim 18, wherein the at least one cationic polymer is chosen from polymers that comprise repeating units of formula (I):

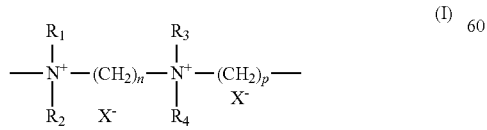

in which $R_1$, $R_2$, $R_3$ and $R_4$, which may be identical or different, are chosen from alkyl and hydroxyalkyl radicals containing from 1 to 4 carbon atoms, n and p are integers ranging from 2 to 20, and $X^-$ is an anion derived from a mineral or an organic acid.

20. The detergent cosmetic composition according to claim 18, wherein the at least one cationic polymer is present in an amount ranging from 0.05% to 10% by weight, relative to the total weight of the composition.

21. The detergent cosmetic composition according to claim 18, wherein the at least one cationic polymer is present in an amount ranging from 0.25% to 3% by weight, relative to the total weight of the composition.

22. The detergent cosmetic composition according to claim 1, wherein the cosmetically acceptable aqueous medium consists of water, or comprises a mixture of water and at least one cosmetically acceptable solvent.

23. The detergent cosmetic composition according to claim 22, wherein the at least one cosmetically acceptable solvent is chosen from $C_1$-$C_4$ lower alcohols, alkylene glycols, and glycerol.

24. The detergent cosmetic composition according to claim 1, wherein the composition comprises at least one adjuvant chosen from cationic surfactants; anionic, nonionic and amphoteric polymers; proteins; protein hydrolysates; ceramides; pseudoceramides; plant oils; fatty acids; hydroxy acids; vitamins; provitamins; volatile and non-volatile silicones, which are soluble or insoluble in the medium; UV-screening agents; moisturizers; antidandruff agents; anti-seborrhoeic agents; hair-loss counteractants; free-radical scavengers; and opacifiers.

25. A method for cleansing and/or removing makeup from keratin materials comprising
  applying to the keratin materials an effective amount of a composition comprising, in a cosmetically acceptable aqueous medium:
  (A) at least one sulfate or sulfonate anionic surfactant;
  (B) at least one carboxylic anionic surfactant other than the surfactant of (A), chosen from polyoxyalkylenated ($C_6$-$C_{24}$)alkyl ether carboxylic acids, polyoxyalkylenated ($C_6$-$C_{24}$)alkylaryl ether carboxylic acids and salts thereof, and polyoxyalkylenated ($C_6$-$C_{24}$)alkylamido ether carboxylic acids and salts thereof;
  (C) at least one amphoteric and/or zwitterionic surfactant, and
  (D) at least one water-insoluble carboxylic acid ester chosen from esters of a $C_3$-$C_{30}$ carboxylic acid and of a $C_1$-$C_{30}$ alcohol, with at least the acid or the alcohol being branched, wherein the total carbon number of the at least one water-insoluble carboxylic acid ester ranges from 12 to 50;
  wherein the at least one sulfate or sulfonate anionic surfactant is present in an amount ranging from 5% to 25% by weight, relative to the total weight of the composition,
  wherein the at least one carboxylic anionic surfactant is present in an amount ranging from 0.5% to 15% by weight, relative to the total weight of the composition,
  wherein the at least one amphoteric and/or zwitterionic surfactant is present in an amount ranging from 0.1% to 20% by weight, relative to the total weight of the composition,
  wherein the at least one water-insoluble carboxylic acid ester is present in an amount ranging from 0.5% to 10% by weight, relative to the total weight of the composition, and
  further wherein the weight ratio of the at least one sulfate or sulfonate anionic surfactant to the at least one carboxylic anionic surfactant ranges from 4 to 10,
  and rinsing off the composition.

26. A process for washing and conditioning keratin materials, comprising
applying to wet keratin materials an effective amount of a composition comprising, in a cosmetically acceptable aqueous medium,
(A) at least one sulfate or sulfonate anionic surfactant,
(B) at least one carboxylic anionic surfactant other than the surfactant of (A), chosen from polyoxyalkylenated ($C_6$-$C_{24}$)alkyl ether carboxylic acids, polyoxyalkylenated ($C_6$-$C_{24}$)alkylaryl ether carboxylic acids and salts thereof, and polyoxyalkylenated ($C_6$-$C_{24}$)alkylamido ether carboxylic acids and salts thereof,
(C) at least one amphoteric and/or zwitterionic surfactant, and
(D) at least one water-insoluble carboxylic acid ester chosen from esters of a $C_3$-$C_{30}$ carboxylic acid and of a $C_1$-$C_{30}$ alcohol, with at least the acid or the alcohol being branched, wherein the total carbon number of the at least one water-insoluble carboxylic acid ester ranges from 12 to 50;
wherein the at least one sulfate or sulfonate anionic surfactant is present in an amount ranging from 5% to 25% by weight, relative to the total weight of the composition,
wherein the at least one carboxylic anionic surfactant is present in an amount ranging from 0.5% to 15% by weight, relative to the total weight of the composition,
wherein the at least one amphoteric and/or zwitterionic surfactant is present in an amount ranging from 0.1% to 20% by weight, relative to the total weight of the composition,
wherein the at least one water-insoluble carboxylic acid ester is present in an amount ranging from 0.5% to 10% by weight, relative to the total weight of the composition, and
further wherein the weight ratio of the at least one sulfate or sulfonate anionic surfactant to the at least one carboxylic anionic surfactant ranges from 4 to 10;
followed by rinsing with water, after an optional leave-in time.

* * * * *